United States Patent [19]
Qiu

[11] Patent Number: 6,077,979
[45] Date of Patent: Jun. 20, 2000

[54] MANUFACTURE OF 3,3',5,5'-TETRAMETHYL-2,2'-BIPHENOL

[75] Inventor: Weiming Qiu, Wilmington, Del.

[73] Assignee: E. I. du Pont de Nemours and Company, Wilmington, Del.

[21] Appl. No.: 09/252,341

[22] Filed: Feb. 18, 1999

[51] Int. Cl.[7] .................................................. C07C 39/12
[52] U.S. Cl. .......................................................... 568/730
[58] Field of Search ............................................... 568/730

[56] References Cited

U.S. PATENT DOCUMENTS

| | | | |
|---|---|---|---|
| 2,490,282 | 12/1949 | Seubold | 568/730 |
| 2,651,644 | 9/1953 | Gisvold | 568/730 |
| 3,929,913 | 12/1975 | Maggioni | 568/730 |
| 4,256,596 | 3/1981 | Cohen | 568/730 |
| 4,380,676 | 4/1983 | Rasberger | 568/730 |

OTHER PUBLICATIONS

H. Raudnitz, *Berichtigung*, 64, 517–518, 1930.
U.S. application No. 09/121,105, filed Jul. 23, 1998.
R.G.R. Bacon et al.,,*J. Chem. Soc.,*, 2275–2280, 1954.
S.L. Cosgrove et al.,*J. Chem. Soc.*, 1726–1730, 1951.
C.G. Haynes et al.,*J. Chem. Soc.*, 2823–2831, 1956.
A.G.M. Barrett et al., *Tetrahedron Letters*, 34, 2233–2234, 1993.
R.G.R. Bacon et al.,*J. Chem. Soc.*, 1339–1344, 1960.

*Primary Examiner*—Michael L. Shippen

[57] ABSTRACT

Coupling in aqueous medium of 2,4-dimethylphenol by persulfate anion or hydrogen peroxide in the presence of iron or iron compounds gives good yields of relatively pure 3,3',5,5'-tetramethyl-2,2'-biphenol.

6 Claims, No Drawings

MANUFACTURE OF 3,3',5,5'-TETRAMETHYL-2,2'-BIPHENOL

FIELD OF THE INVENTION

The manufacture of 3,3',5,5'-tetramethyl-2,2'-biphenol in high yield is accomplished by the coupling of 2,4-dimethylphenol caused by a combination of iron or iron compound and persulfate anion or hydrogen peroxide in aqueous medium.

TECHNICAL BACKGROUND

Biphenols, including substituted biphenols are known compounds, and are used as chemical intermediates and as monomers. 3,3',5,5'-Tetramethyl-2,2'-biphenol (TMBP) is similarly useful, see for example U.S. patent application Ser. No. 121,105, filed Jul. 23, 1998. Biphenols can be made by the oxidative coupling of (mono)phenols, but often many different products are obtained, other types of products such as ketones are obtained, and/or overall yields are poor for other reasons. This reaction is particularly useful where the phenol is substituted with electron donating groups.

Various oxidants may be used for the oxidative coupling of phenols, and one useful combination of reagents is a transition metal and an oxidizing agent, such as persulfate anion, see for instance R. G. R. Bacon et al., J. Chem. Soc., p. 2275–2280 (1954); S. L. Cosgrove et al., J. Chem. Soc., p. 1726–1730 (1951); C. G. Haynes et al., J. Chem. Soc., p. 2823–2831 (1956); and A. G. M. Barrett et al., Tetrahedron Letters, vol. 34, p. 2233–2234 (1993). The oxidation of 2,4-dimethylphenol (DMP) to TMBP has also been carried out by similar procedures and for the most part the yields of the desired TMBP have been low to moderate. It is noted that some of the oxidants and/or cocatalysts involve the use of relatively expensive metal compounds, which is a disadvantage for large scale commercial use.

R. G. R. Bacon et al., J. Chem. Soc., p. 1339–1344 (1960) report the preparation of TMBP from DMP in relatively low yield using a combination of persulfate anion and silver cation. No mention is made of using iron in place of the more expensive silver.

SUMMARY OF THE INVENTION

This invention concerns a process for the production of 3,3',5,5'-tetramethyl-2,2'-biphenol, comprising, contacting in an aqueous medium at a temperature of about 0° C. to about 100° C., 2,4-dimethylphenol, an oxidant selected from the group consisting of persulfate anion and hydrogen peroxide, and a catalytically effective amount of iron or an iron compound.

DETAILS OF THE INVENTION

The process described herein is run in aqueous medium, that is liquid water. Small amounts (up to 25 volume percent) of other "solvents" may be present in the medium, but it is preferred that the medium be pure water, with of course other process ingredients. The process is carried out at about 0° C. to about 100° C., preferably about 15° C. to about 50° C.

The persulfate anion may be added as part of any inorganic persulfate that, preferably, has some solubility in water. Preferred persulfates are ammonium persulfates and alkali metal persulfates. Ammonium, sodium or potassium persulfates are especially preferred. Hydrogen peroxide may be added as an aqueous solution, preferably an aqueous solution containing between 3 percent and 55 percent of hydrogen peroxide by weight. Persulfate anion is a preferred oxidant.

DMP is commercially available from Aldrich Chem. Co., Milwaukee, Wis.

The iron may be added in the form of metallic iron or a compound of iron. If iron metal is added, it may be used in the form of "pure" iron or iron in the form of an alloy from which iron may be extracted by the aqueous medium of the process. It is believed that if iron metal (or an alloy) are present, a "small amount" of iron is oxidized and extracted into the process medium. If an iron compound is used, the iron may be in the +2 or +3 form. It is preferred that any iron compound used be an inorganic compound such as iron sulfate or iron chloride.

Although not critical, it is preferred that the molar equivalent ratio of DMP:oxidant is about 1.2:1.0 to about 1.0:1.2, more preferably about 1.0. This results in the most efficient usage of DMP and oxidant on a stoichiometric basis. The amount of iron present is not critical; a catalytically effective amount is present. By catalytically effective amount is meant an amount that will cause at least 25 percent of the DMP to have reacted at the temperature of the process in 100 hours or less. A useful range of iron compound is about 0.05 to about 10 mole percent of iron, based on the amount of DMP added, more preferably about 0.2 to about 5 mole percent.

As described in Example 1, the product may simply be filtered from the aqueous medium in relatively pure form. If further purification is desired, it may be recrystallized from an appropriate solvent.

In the Examples, "RT" is room temperature. References to the "product" and/or "biphenol" are to 3,3',5,5'-tetramethyl-2,2'-biphenol.

EXAMPLE 1

Coupling 2,4-Dimethylphenol Using Sodium Persulfate and Ferrous Sulfate

A 5 L flask equipped with a mechanical stirrer, and an addition funnel was charged with 2,4-dimethylphenol (122 g, 1.0 mol), $FeSO_4 \cdot 7H_2O$ (13.9 g), and water (1.5 L) at RT. Sodium persulfate (238 g) in 1 L of water was added to the above mixture at RT over 4 h. The resulting mixture was stirred at RT for 2 days. The precipitated solid was collected by filtration, washed with water (3×500 ml), and dried under vacuum at 50° C. for a day to give 114 g of the product, 94% yield. Both GC-MS and NMR analysis indicated that it had about 95% purity. $^{13}C$ NMR($CDCl_3$): 16.1, 20.4, 122.1, 125.2, 128.5, 130.0, 132.0, 149.2 ppm. $^1H$ NMR($CDCl_3$): 2.30 (s, 12H), 5.10 (s, 2H), 6.90 (s, 2H), 7.08 (s, 2H) ppm.

EXAMPLE 2

Coupling 2,4-Dimethylphenol Using Sodium Persulfate and Ferrous Sulfate

A mixture of 2,4-dimethylphenol (0.15 g), $FeSO_4$ (0.05 mol), $Na_2S_2O_8$ (0.31 g), and 20 ml water was stirred at RT for 2 days. The reaction mixture was extracted by ether (20 ml). Analysis of the ether solution indicated 95% conversion and 92% selectivity to the biphenol product. The ether solution was concentrated to give 0.15 g yellow solid. NMR analysis of this sample indicated that it contained small amounts of ether, water, and starting phenol and other unsolved impurity peaks; but overall the sample was relatively pure desired biphenol product.

COMPARATIVE EXAMPLE A

Coupling 2,4-Dimethylphenol Using Sodium Persulfate and Silver Nitrate

A mixture of 2,4-dimethylphenol (0.122 g, 1 mmol), sodium persulfate (0.24 g, 1 mmol), $AgNO_3$ (1 ml, 0.05 M), and water (1 ml) was stirred at RT for 2 days. Brown solid was precipitated. The mixture was extracted by ether (6 ml). Analysis of the ether solution indicated about 75% conversion and 90% selectivity to the biphenol product.

COMPARATIVE EXAMPLE B

Coupling 2,4-Dimethylphenol Using Oxone® and Ferrous Sulfate

A mixture of 2,4-dimethylphenol (0.122 g, 1 mmol), Oxone® (0.14 g, a mixture of potassium peroxymonosulfate, potassium bisulfate and potassium sulfate available from E. I. du Pont de Nemours and Company, Wilmington, Del. USA), $FeSO_4 \cdot 7H_2O$ (1 ml, 0.05 M), and water (1 ml) was stirred at RT for 50 hours. The mixture was extracted by ether (3 ml). Analysis of the ether solution indicated about 57% conversion and 96% selectivity to the biphenol product.

EXAMPLE 3

Coupling 2,4-Dimethylphenol Using Hydrogen Peroxide and Ferric Chloride

To a mixture of 2,4-dimethylphenol (0.122 g, 1 mmol) and $FeCl_3$ (1 ml, 0.05 M) was added hydrogen peroxide (0.10 g, 30%, in 1 ml water) dropwise at 5° C. The mixture was stirred at 5° C. for 16 h, then at RT for 2 h. The mixture was extracted with ether (3 ml). Analysis of the ethers solution indicated an 80% conversion of starting phenol and 95% selectivity to 3,3',5,5'-tetramethyl-2,2'-biphenol.

COMPARATIVE EXAMPLE C

Coupling 2,4-Dimethylphenol Using Sodium Persulfate and $Co(OH)_2$

A mixture of 2,4-dimethylphenol (0.12 g, 1 mmol), $Co(OH)_2$ (0.05 mol), $Na_2S_2O_4$ (0.24 g, 1 mmol), and 2.5 ml water was stirred at RT for 2 days. The reaction mixture was extracted by ether (4 ml). Analysis of the ether solsution indicated about 27% conversion and 90% selectivity to the biphenol product.

EXAMPLE 4

Coupling 2,4-Dimethylphenol Using Sodium Persulfate and Ferric Chloride Catalyst A mixture of 2,4-dimethylphenol (0.12 g), $FeCl_3$ (0.05 mmol), $Na_2S_2O_8$ (0.24 g), and 2.5 ml water was stirred at RT for 2 days. The reaction mixture was extracted by ether (4 ml). Analysis of the ether solution indicated about 83% conversion and 95% selectivity to the biphenol product.

EXAMPLE 5

Coupling 2,4-Dimethylphenol Using Sodium Persulfate and Iron Powder

A mixture of 2,4-dimethylphenol (0.12 g), Fe (5 mg), $Na_2S_2O_8$ (0.24 g), and 2 ml water was stirred at RT for 2 days. The reaction mixture was extracted by ether (4 ml). Analysis of the ether solution indicated about 80% conversion and 90% selectivity to the biphenol product.

What is claimed is:

1. A process for the production of 3,3',5,5'-tetramethyl-2,2'-biphenol, comprising, contacting in an aqueous medium at a temperature of about 0° C. to about 100° C., 2,4-dimethylphenol, persulfate anion, and a catalytically effective amount of iron or an iron compound.

2. The process as recited in claim 1 wherein said temperature is about 15° C. to about 50° C.

3. The process as recited in claim 1 wherein said persulfate anion is present as ammonium, sodium, or potassium persulfate.

4. The process as recited in claim 1 wherein a molar ratio of said oxidant to said 2,4-dimethylphenol is about 1.0.

5. The process as recited in claim 1 wherein said iron is present as an inorganic iron compound.

6. The process as recited in claim 5 wherein said inorganic iron compound is present in an amount of about 0.05 to about 10 mole percent of said 2,4-dimethylphenol.

* * * * *